United States Patent [19]

Stücker et al.

[11] Patent Number: 5,713,898
[45] Date of Patent: Feb. 3, 1998

[54] ORTHOPEDIC SURGICAL HOLDING DEVICE

[75] Inventors: Ralf Stücker, Waldkirch; Günther Rehder, Winterbach; Bernd Schäfer, Schorndorf, all of Germany

[73] Assignee: Schafer micomed GmbH, Schorndorf, Germany

[21] Appl. No.: 545,575

[22] PCT Filed: May 18, 1994

[86] PCT No.: PCT/EP94/01606

§ 371 Date: Jan. 29, 1996

§ 102(e) Date: Jan. 29, 1996

[87] PCT Pub. No.: WO94/26194

PCT Pub. Date: Nov. 24, 1994

[30] Foreign Application Priority Data

May 18, 1993 [DE] Germany ............... 43 16 541.9
Sep. 22, 1993 [DE] Germany ............... 9314294 U

[51] Int. Cl.[6] ................................................ A61B 17/58
[52] U.S. Cl. ..................... 606/60; 606/61; 606/70; 606/72; 606/73
[58] Field of Search ..................... 411/103, 104, 411/105, 108, 109, 110; 606/61, 60, 69, 72, 73

[56] References Cited

U.S. PATENT DOCUMENTS

| 4,408,601 | 10/1983 | Wenk | 606/69 |
| 4,493,317 | 1/1985 | Klaue | 606/69 |
| 5,176,678 | 1/1993 | Tsou | 606/61 |
| 5,234,431 | 8/1993 | Keller | 606/61 |
| 5,257,993 | 11/1993 | Asher et al. | 606/61 |
| 5,290,288 | 3/1994 | Vignaud et al. | 606/69 |
| 5,443,467 | 8/1995 | Biedermann et al. | 606/72 |
| 5,487,743 | 1/1996 | Laurain et al. | 606/61 |
| 5,496,321 | 3/1996 | Puno et al. | 606/61 |
| 5,536,268 | 7/1996 | Griss | 606/61 |
| 5,549,607 | 8/1996 | Olson et al. | 606/61 |
| 5,562,663 | 10/1996 | Wisnewski et al. | 606/61 |

FOREIGN PATENT DOCUMENTS 0 443 894 A1  8/1991  European Pat. Off. .

Primary Examiner—Michael Buiz
Assistant Examiner—Julian W. Woo
Attorney, Agent, or Firm—Jones, Tullar & Cooper, P.C.

[57] ABSTRACT

In an orthopedic surgical holding device for a correcting rod, having a bone plate which can be fastened on the bone, a receiver device for the correcting rod and a fixing device maintaining the correcting rod in the receiver device. An optimal transfer of the occurring forces and moments is achieved in that the bone plate can be fixed independently of the receiver device (10) and has a bearing for the receiver device, and in that the receiver device can be pushed into the bearing from the proximal side and in the course of this extends through the bone plate and extends beyond it on the distal side for receiving the correcting rod.

23 Claims, 4 Drawing Sheets 5,713,898

ORTHOPEDIC SURGICAL HOLDING DEVICE

FIELD OF THE INVENTION

The present invention relates to an orthopedic surgical holding device for a correcting rod, having a bone plate which can be fastened on the bone, a receiver device for the correcting rod and a fixing device for maintaining the correcting rod in the receiver device.

BACKGROUND OF THE INVENTION

Numerous orthopedic surgical holding devices are known. As a rule, bone screws are employed for the fixing of individual bones in cases of deformations or fractures, which are screwed into the bones or bone segments and are connected with each other by means of correcting rods. As a rule, these bone screws consist of a threaded shaft and a screw head, wherein the threaded shaft is screwed into the bone until the screw head rests on the surface of the bone. This position of the bone screw is desirable because in this position it is possible to transfer maximal tension and pressure forces as well as moments to the bone. Since, as a rule, the screw head of the bone screw is embodied as a fork head, the bone screw must be rotated to a position in which the groove between legs of the fork head is oriented in the direction of the correcting rod to be received. However, because of this requirement it is not always assured that the bone screw is screwed completely in until the screw head rests on the bone surface. Depending on the thread pitch, the screw head is at a more or less large distance from the bone surface, because of which on the one hand the force of the tension and pressure forces is reduced and, on the other hand, the danger of damage to the bone during force peaks is increased.

If there is a bone plate between the screw head and the bone, and if this bone plate is also fixed via the bone screws, it is not always assured that the bone plate, which has the function of evenly distributing the forces acting on the bone screw, is always pressed by means of the bone screw free of play and resting flush against the surface of the bone. If the bone plate rests against the bone with play, there is even the danger of irritation of the bone, which slows down the healing process. The bone plate is fixed without play on the bone by the screw head of the bone screw only when the desired turning position of the bone screw, which depends on the orientation of the correcting rod, is accidentally taken up at the time the maximum screw-in depth has been reached.

OBJECT AND SUMMARY OF THE INVENTION

It is therefore an object of the present invention to further develop a holding device of the above mentioned type so that by means of it the bone plate rests without play against the bone, regardless of the rotated position of the receiver device for the correcting rod.

This object is attained in accordance with the present invention in that the bone plate can be fixed independently of the receiver device and has a bearing for the receiver device, and in that the receiver device can be pushed into the bearing from the proximal side and in the course of this extends through the bone plate and extends beyond it on the distal side for receiving the correcting rod.

By means of the embodiment in accordance with the present invention of the holding device, wherein the bone plate can be fixed on the bone independently of the receiver device which, for example, takes place via two or more screws, the advantage is gained that the correcting forces or moments are transmitted free of play from the bone plate to a large area of the bone. Since the fixing of the bone plate is independent of the receiver device, the position or the orientation of the correcting rod is of no consequence.

The receiver device is connected with the bone plate by insertion from the proximal side, i.e. from the side which rests against the surface of the bone, and is held by a bearing of the bone plate. The receiver device extends beyond the distal side of the bone plate and can receive the correcting rod there. In an advantageous manner the receiver device is disposed rotatable in the bearing over a plurality of steps or continuously. By means of this it is possible to align the receiver device exactly in the direction of the correcting rod, while the turned position is independent of the fixing of the bone plate.

In accordance with an exemplary embodiment of the present invention, the bone plate has a circular through opening, in which the receiver device is maintained immovably. In contrast thereto, in accordance with a further preferred exemplary embodiment of the present invention, the receiver device is crosswise displaceable in the bearing in one direction. In this way it is not necessary to align three or more bone plates, which are intended to be connected by a single correcting rod, exactly with each other, which would be difficult anyway. Instead, in this way it is possible not only to rotate the receiver devices, but also to displace them in one axial direction in order to obtain the exact alignment of three or more such receiver devices. This permits less strenuous efforts in aligning and fixing the bone plates on the bone.

With the last mentioned further preferred embodiment it is structurally practical for the bone plate to have a through opening in the shape of an elongated hole, in which the receiver device is maintained so it is movable crosswise, and to embody the bearing also in the shape of an elongated hole corresponding to the through opening.

Preferably, the receiver device terminates flush with the bone plate on its proximal side or is disposed to be recessed. By means of this it is assured that turning of the receiver device for alignment when the bone plate has been screwed on does not lead to damage of the bone surface. In addition, when disposed flush or arranged in a recessed manner, the receiver device does not get in the way of screwing down the bone plate.

In a preferred further development it is provided that the bone plate has a plurality of bearings for a corresponding plurality of receiver devices. This is the case in particular with larger bone plates, wherein a correcting rod has to be fixed at several places or wherein several correcting rods are disposed on the bone plate. Here, too, the several receiver devices can be aligned individually on the respective correcting rod without the bone plate being affected.

The receiver device is preferably embodied as a fork head and has a radially projecting collar on its end to be anchored in the bone plate which grips the bearing of the bone plate from behind. The collar gripping the bearing from behind prevents the receiver device from being pulled through the bone plate and simultaneously represents the rotary bearing of rotatable receiver devices. In connection with this, the collar can be circular or polygonal wherein, as already mentioned, a continuous turning is possible with the circular shape and, with a pentagonal or heptagonal shape, a corresponding number of rotated positions is possible.

In a further development of the present invention, a coupling ring is provided which receives the receiver device.

In the previously mentioned first exemplary embodiment of the present invention, the coupling ring is disposed to rest on the distal side of the bone plate, and the surface of the coupling ring resting against the bone plate and the distal side of the bone plate are provided with a radial front serration (Hirth serration). However, in accordance with the previously mentioned second exemplary embodiment, an intermediate ring is provided which receives the receiver device, wherein the intermediate ring is suitably disposed between the distal side of the bone plate and the proximal side of the coupling ring. In this case, front faces of the coupling ring and the intermediate ring which rest on each other are provided with a radial front serration (Hirth serration), while the surface of the intermediate ring resting against the bone plate and the distal side of the bone plate have front serrations which enclose the bearing which is in the shape of an elongated hole and which are respectively formed by parallel notches extending crosswise to the long extension of the bearing. Security against twisting of the coupling ring with respect to the bone plate is provided in this way either directly or indirectly via the intermediate ring. In contrast to this, the parallel notches of the second exemplary embodiment of the present invention provide, by means of the intermediate ring, the fixing of the displaced position of the receiver device with respect to the bone plate.

With the previously mentioned second embodiment of the present invention, a connection which is secure against relative rotation but is axially moveable is additionally provided between the receiver device and the coupling ring to assure that the fork head of the receiver device is also fixed by the indirect fixing of the coupling ring. This takes place in a simple manner in that the receiver device has an axial groove on at least one circumferential place, which is immovably engaged by a pin or the like which extends through a radial bore of the coupling ring.

In addition, the distal side of the coupling ring has a diagonal groove for receiving the correcting rod. With the correcting rod inserted into the receiver device, the former is seated in the diagonal groove of the coupling ring and is additionally enclosed by the two legs of the fork head of the receiver device. In this way the direction of the coupling ring and thus the fork head is fixed via the front serration and the diagonal groove.

In an advantageous manner, the diagonal groove is provided with longitudinal notches which are free of undercuts, into which the correcting rod, provided with longitudinal grooves corresponding to the longitudinal notches, can be inserted.

For fastening the correcting rod in the receiver device, the fixing device has a head nut, in particular a cap nut, which can be screwed on the receiver device embodied as a fork head. The correcting rod is fixed in the receiver device by means of this screwable head nut in such a way, that the occurring tension and pressure forces as well as the moments can be transmitted to the receiver device and from there to the bone plate.

Preferably, the head nut is provided with a coaxially screwed in fixing screw, in particular with a hexagon socket and/or a cup point. The fixing screw can be adjusted by means of the hexagon socket after the head nut has been screwed on, and can be screwed on the inserted correcting rod in such a way that the cup point digs into the material of the correcting rod. In this way fixing against displacement as well as twisting is provided.

In a further development it is provided that the bone plate has at least two fastening bores, which are located opposite each other with respect to the bearing, for receiving bone screws. The bone plate is fixed on the bone by means of these bone screws, the fastening bores being used for receiving the screw heads of the bone screws.

In an advantageous manner, the proximal indentation is here disposed orthogonally to the surface of the bone plate, and the distal fastening bore is obliquely disposed, so that the bone screws converge. This has the advantage that the bone plate can still be fastened securely even in relatively small bones and that the screws do not protrude from the other side of the bone immediately after having been screwed with.

In a particularly preferred further development the fastening bores have a cup-shaped bearing for the screw head of the bone screw. By means of this the possibility is provided that the bone screw need not be screwed in exclusively orthogonally in respect to the bone plate, but instead can take up slightly oblique positions, so that regardless of the position of the bone plate, the screw shaft can be turned into areas of the bone in which it can find optimum support.

Further advantages, characteristics and details of the invention ensue from the following description, wherein two preferred exemplary embodiments are illustrated, making reference to the drawings. In this connection it is possible that the characteristics shown in the drawings and mentioned in the description can be embodied respectively individually by themselves or in arbitrary combinations in the invention.

DETAILED DESCRIPTION OF THE PREFERRED EMBODIMENTS

Figure 1:
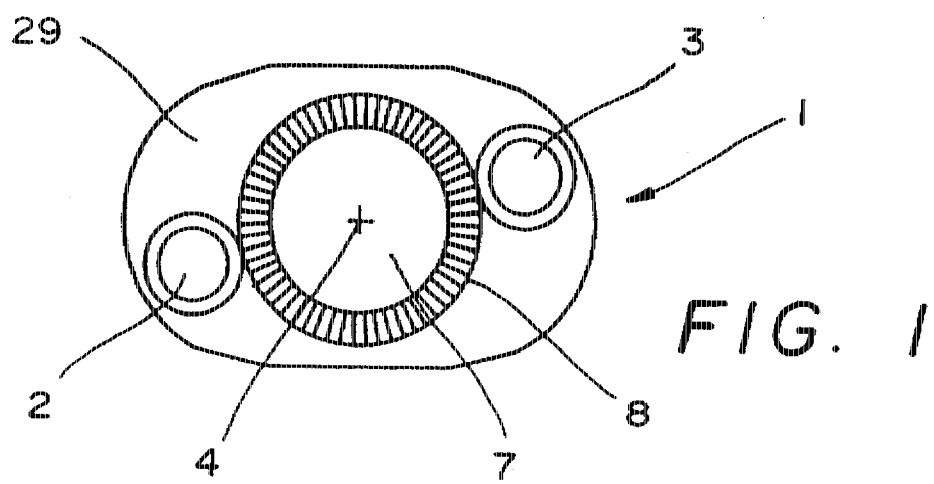
FIG. 1 is a top view of a bone plate of the holding device of FIG. 6.

FIG. 1 shows a top view of a bone plate 1 of an orthopedic surgical holding device (FIG. 6) in accordance with the first exemplary embodiment of the present invention, wherein the two fastening bores 2 and 3 can be seen, via which the bone plate 1 can be fastened on the bone by means of appropriate bone screws. In a preferred manner, the two fastening bores 2 and 3 are disposed opposite each other with respect to the center 4 of the bone plate 1. The fastening bores 2 and 3 respectively have a cup-shaped bearing 5, which can be clearly seen in FIG. 6. The screw head of a bone screw, not shown, which is embodied to be correspondingly spherical, is received in this cup-shaped bearing 5. The bearing 5 has the advantage that it is not absolutely necessary to align the bone screw coaxially with the fastening bore 2 or 3, but instead it can take up slightly oblique positions, so that the bone screw can be screwed into suitable areas of the bone.

Figure 6:
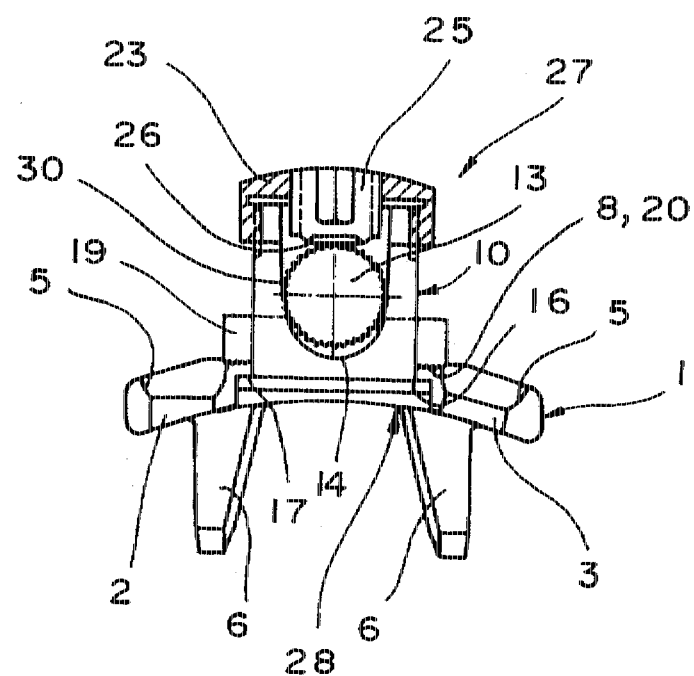
FIG. 6 is a partially sectional lateral view of an orthopedic surgical holding device with the correcting rod inserted, in accordance with a first exemplary embodiment of the present invention.

It can furthermore be seen from FIG. 6, that the fastening bore 3 is placed obliquely in relation to the fastening bore 2, the axis of the fastening bore 3 extending orthogonally in respect to the bone plate 1 and the axis of the fastening bore 2 extending parallel to the anchor pins 6.

Furthermore, it can be seen from FIG. 1 that the bone plate 1 is provided with a central opening 7 which, in the embodiment illustrated in FIG. 1, is circular. This opening 7 is surrounded by a radial front serration 8 provided in the distal top side of the bone plate 1.

Figure 2:
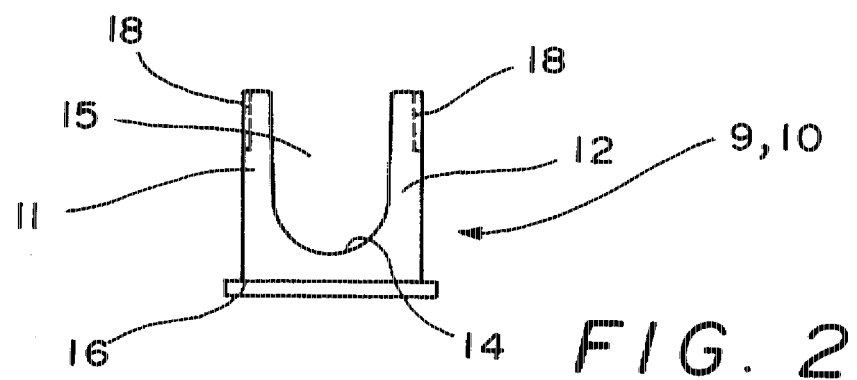
FIG. 2 is a lateral view of a fork head of the holding device of FIG. 6.

A receiver device 10 embodied as a fork head 9 is shown in FIG. 2 and has an essentially U-shaped form. In this case the two legs 11 and 12 form a receiver for a correcting rod 13 (FIG. 6), which comes to lie close to the bottom 14 of the groove 15 formed between the legs 11 and 12. The upper section of each leg 11 and 12 is provided with an exterior thread 18. On its underside the fork head 9 has a radially projecting collar 16 which grips a bearing 17 on the underside of the bone plate 1 from behind (FIG. 6).

Figure 3:
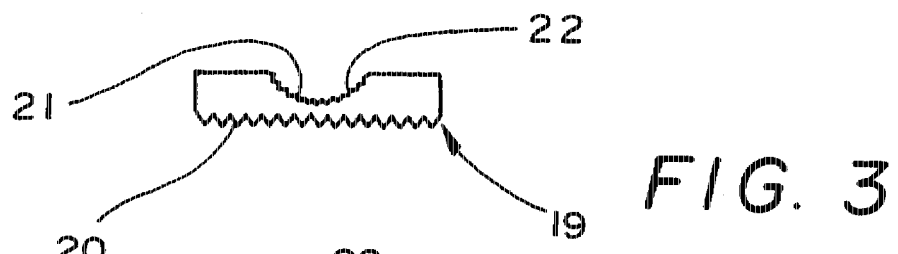
FIG. 3 is a lateral view of a coupling ring of the holding device of FIG. 6.

FIG. 3 shows a coupling ring 19 provided on its underside with a radial front serration 20, corresponding to the front serration 8. The top has a diagonal groove 21 provided with longitudinal grooves 22 (FIG. 4) free of undercuts.

Figure 5:
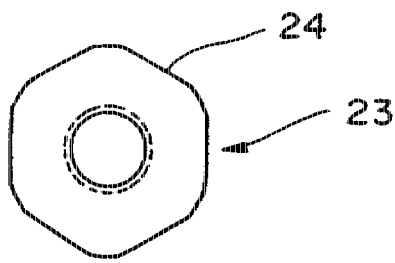
FIG. 5 is a top view of the head screw of the holding device of FIG. 6.

FIG. 5 shows a top view of a head nut 23, shown in cross section in FIG. 6, which is screwed on the exterior thread 18 of the fork head 9. The head nut 22 has an exterior hexagonal shape 24 and is spherical on its top. A fixing screw 25 (FIG. 6) is coaxially screwed into the head nut 23. This fixing screw 25 is embodied as a hexagonal socket with a spherical top and has, on the side resting on the correcting rod 13, a cup point 26. The fixing screw 25 and the head nut 23 comprise the fixing device 27 for the correcting rod 13.

Figure 7:
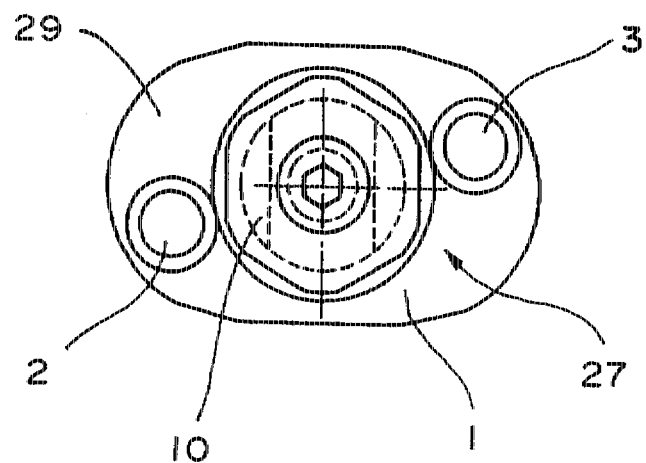
FIG. 7 is a top view of the holding device of FIG. 6.

The top view of the holding device in accordance with the present invention of FIG. 7 shows the crowded and space-saving disposition of the individual elements on the bone plate 1. It should be stressed that symmetry is maintained. The symmetrical disposition is not absolutely required, but should be attempted.

The use of the individual elements will be briefly explained in what follows. Prior to screwing down the bone plate 1 on the bone to be treated, the fork head 9 is inserted from the proximal side 28 far enough that the collar 16 rests against the bearing 17. Then the bone plate 1 is fastened on the bone by means of appropriate bone screws. By turning around its axis, the fork head 9 is aligned in such a way that the correcting rod 13 can be inserted into the groove 15 between the two legs 11 and 12. Prior to inserting the correcting rod 13, the coupling ring 19 is pushed on the fork head 9 in such a way that the diagonal groove 21 is aligned in the direction of the groove 15. In the course of this the front serration 21 of the coupling ring 19 engages the front serration 8 of the distal side in the bone plate 1. After pushing the coupling ring 19 on and aligning it, the correcting rod 13 is inserted into the receiver device 10, at which time it is still possible to correct the turned position of the fork head 9 and the turned position of the coupling ring 19. The receiver device 10 is closed at the top by means of the head nut 23 which is screwed on the exterior thread 18. Fixing of the correcting rod 13 is performed by means of the fixing screw 25 which is screwed into the head nut 23. In the course of this the cup point 26 digs into the longitudinal grooves 30 which are embodied to correspond to the longitudinal notches 22.

It can be clearly seen from FIG. 6 that the correcting rod 13 does not rest on the bottom 14 of the groove 13, but on the longitudinal notches 22 of the diagonal groove 21 of the coupling ring 19. Because of the tightening of the fixing device 27, on the one hand the fork head 9 is drawn into the bearing 17, on the other hand the correcting rod 13 is pushed into the diagonal groove 21 and, because of this, the coupling ring 19 is pushed into the front serration 8 of the distal side 29 of the bone plate 1. The receiver device 10 is fixed against the bone plate 1. In addition, the correcting rod 13 is secured against shifting as well as against turning around the rod axis by the longitudinal notches 22 and the longitudinal grooves 30. Finally, the correcting rod 13 is secured against turning around the axis of the center 4, which is accomplished by the front serrations 8 and 20.

The individual setting or adjustment of the receiver device 10 is of advantage in the holding device of the present invention, wherein it is assured that the tension and pressure forces as well as the moments of the correcting rod 13 are directly transmitted to the bone plate 1 and from there to the bone.

Figure 8:
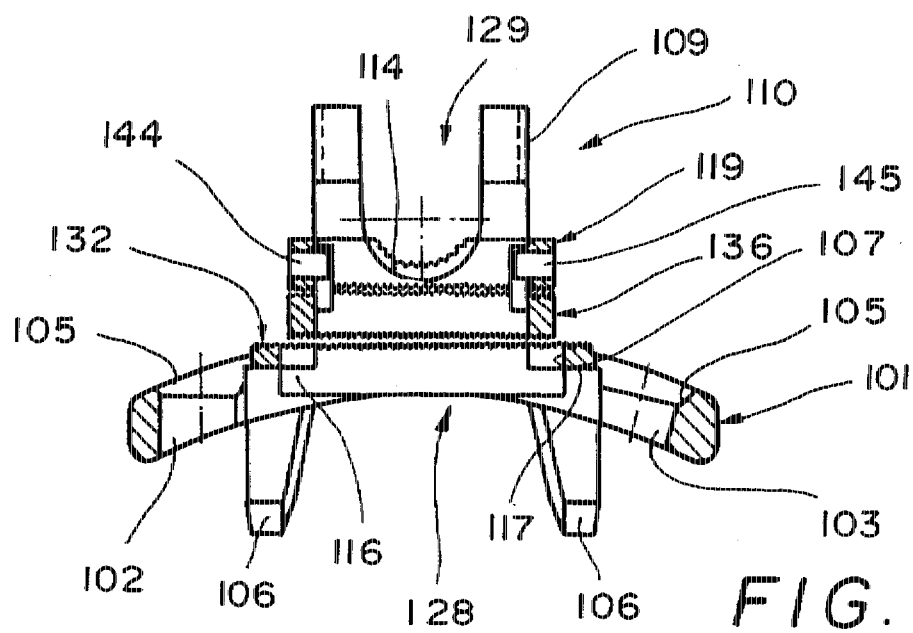
FIG. 8 is a partially sectional lateral view of an orthopedic surgical holding device without the correcting rod inserted and without the head nut screwed on, in accordance with a second exemplary embodiment of the present invention.
Figure 9:
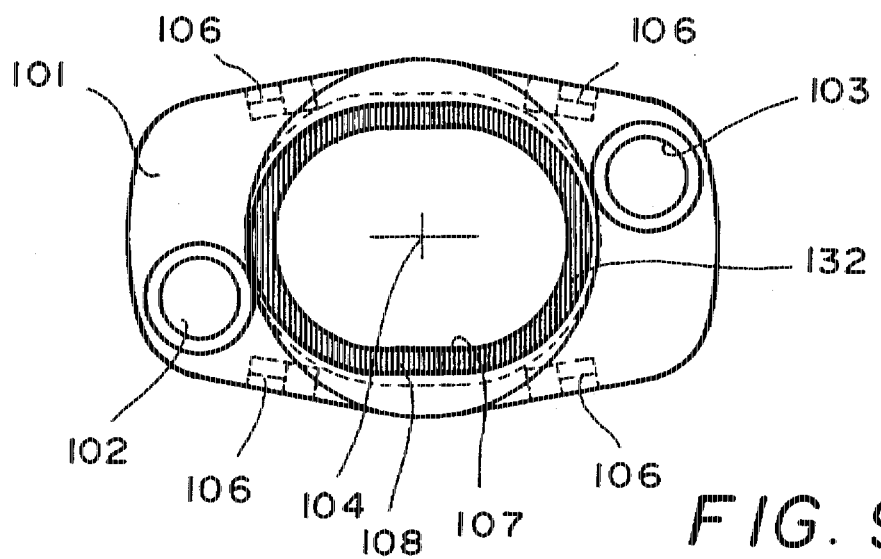
FIG. 9 is a top view of the bone plate of the holding device of FIG. 8.
Figure 10:
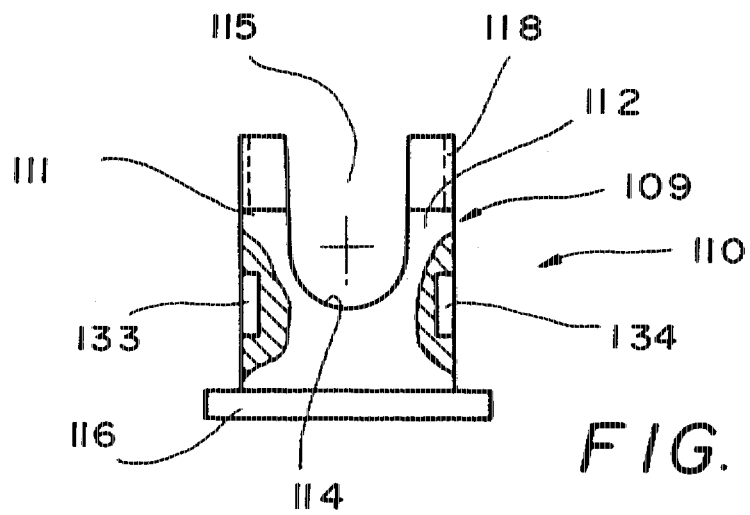
FIG. 10 is a partially broken-open lateral view of the fork head of the holding device of FIG. 8.

In the description of the second exemplary embodiment of the orthopedic surgical holding device illustrated in FIG. 8, corresponding reference numerals, which are preceded by the number "1", are used for like parts or elements. However, the insertable correcting rod 13 and the fixing device 27 have been omitted in FIG. 8 for the sake of simplicity. The holding device illustrated in FIG. 8 has, besides a bone plate 101, a receiver device 110, a coupling ring 119 and the fixing device, not shown, an intermediate ring 136 threaded on the fork head 109 of the receiver device 110 between the coupling ring 119 and the bone plate 101, which here is provided with four anchor pins 106.

The bone plate 101 has a basic shape corresponding to the bone plate 1 shown in FIG. 1, with two fastening bores 102 and 103, but is provided with an opening 107 embodied as an elongated hole, the greater width of which lies in the longitudinal extension of the bone plate 101. A front face 132 serrated by means of parallel notches 108 is provided around the elongated holes 107 from the direction of the distal side 129 of the bone plate 1. The parallel notches 108 extend in the direction of the narrow side of the bone plate 101, i.e. crosswise to the longitudinal extension of the bone plate 101 or the elongated hole 107.

In its essential structure, the receiver device 110 embodied as a fork head 109 corresponds to the receiver device 10 shown in FIG. 2. The only difference lies in that it is provided with two diagonally opposite, axially extending grooves 133, 134. The fork head 109 is, the same as its collar 116 with a larger diameter, circular in cross section in such a way that the receiver device 110 can be inserted into the elongated hole 108 of the bone plate 101 from the direction of the proximal side 128, wherein the collar 116 is received in an oval bearing 117 corresponding to the shape of the elongated hole 107. It is possible in this way to move the receiver device 110 in the elongated hole opening 107 of the bone plate 101 in the direction of the longitudinal extension of the bone plate 101. The receiver device 110 is fixed in the crosswise direction of the bone plate 101.

Figure 11:
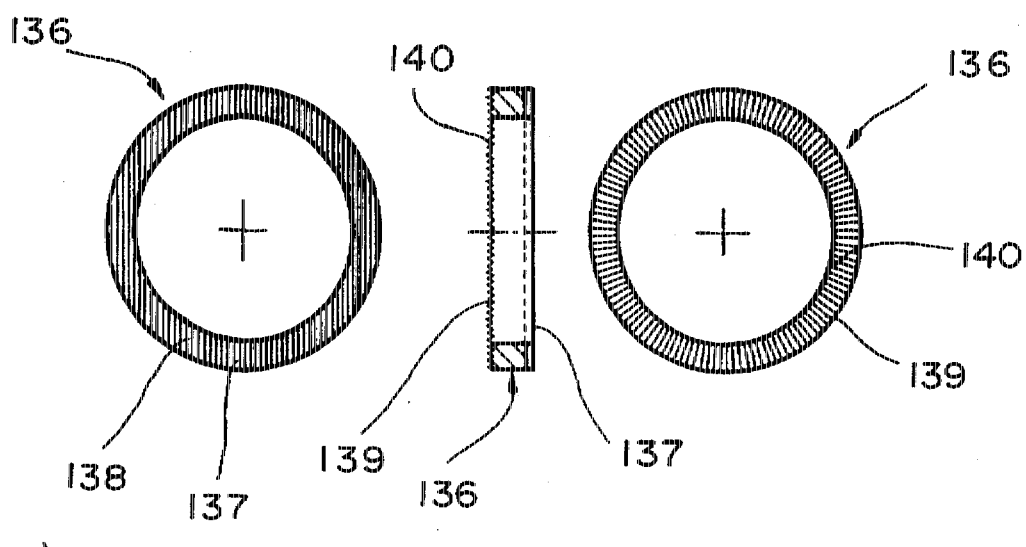
FIG. 11 is a bottom view, a longitudinal section and a top view of an intermediate ring of the holding device of FIG. 8.

FIG. 11 shows the intermediate ring 136 which can be pushed over the fork head 109 and the proximal or underside 137 of which is provided with parallel notches 138, and the distal or top side 139 of which is provided with a radial front serration (Hirth serration) 140.

Figure 4:
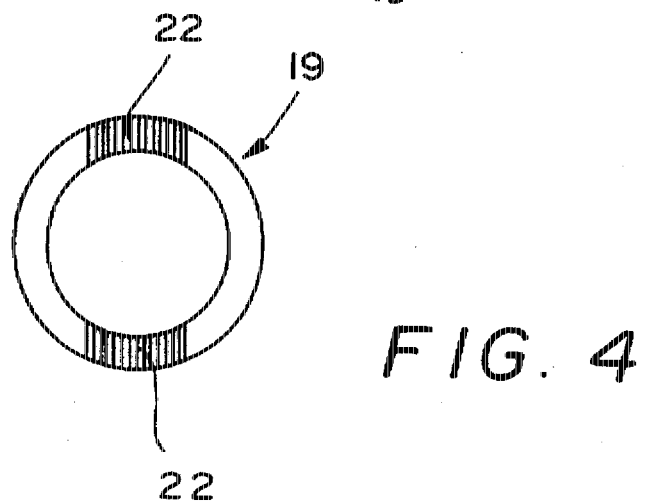
FIG. 4 is a top view of the coupling ring of FIG. 3.
Figure 12:
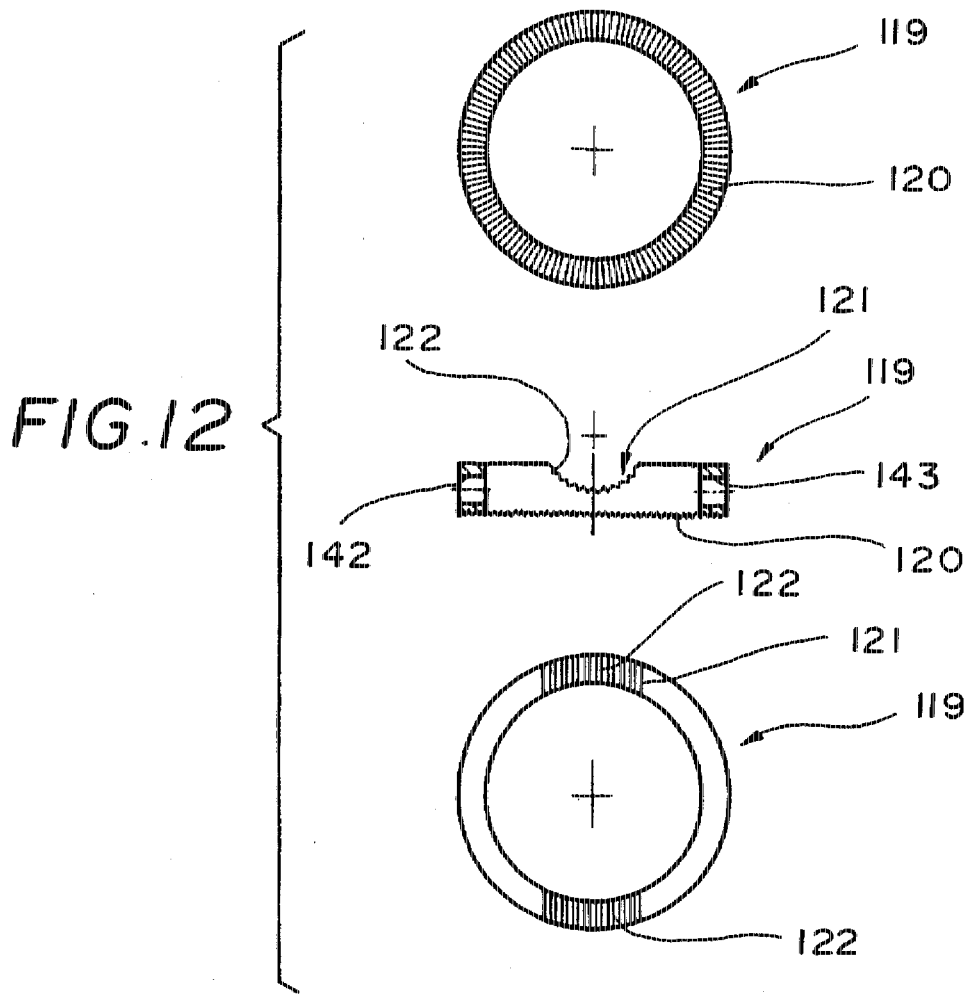
FIG. 12 is a bottom view, a longitudinal section and a top view of an coupling ring of the holding device of FIG. 8.

The coupling ring 119 shown in FIG. 12 essentially has the shape of the coupling ring 19 of the first exemplary embodiment illustrated in FIGS. 3 and 4, with the only additional step that it is provided with two diagonally opposed bores 142 and 143 on its circumference.

As shown by FIG. 8, the receiver device 110 is inserted in the assembled state into the bone plate 101 from the direction of the proximal side before the anchor pins 106 of the bone plate 101 are hammered into a bone and fastened with the aid of fastening screws, not shown. First, the intermediate ring 136 is threaded on the fork head 109 of the receiver device 110 in such a way that the notches 138 provided on the underside 137 can engage the parallel notches 108 of the front face 132 of the bone plate 101 surrounding the elongated hole opening 107. Before these parallel notches 108 and 138 are brought into engagement with each other, the receiver device 110 with the intermediate ring 136 is moved or displaced in the longitudinal direction of the bone plate 101 into its desired position. After that, the coupling ring 119 is pushed over the fork head 109, as in the first exemplary embodiment, the radial front serration 120 of which can engage, after a rotating displacement, the front serration 140 of the intermediate ring 136. Pins 144 and 145 are inserted into the bores 142 and 143 of the coupling ring 119, which immovably engage the respective axial groove 133, 134 at the outer circumference of the fork head 109 in the circumferential direction and in this way make a connection fixed against relative rotation between the coupling ring 119 and the receiver device 110. In this way, following a corresponding turning of the receiver device 110 into the correct position in relation to a correcting rod to be received, the fork head 109 can be fixed secure against relative rotation on the intermediate ring 136 by means of the coupling ring 119, when the fixing device, not shown, has been applied after the insertion of a correcting rod, also not shown, and has been tightened.

Thus, by means of the design of the second exemplary embodiment of the orthopedic surgical holding device it is not only possible to turn the fork head 109 in relation to the vertical axis, but also to displace it in the longitudinal direction of the bone plate 101, so that a correcting rod can be placed over three or more holding devices without it being necessary to bring the respective bone plates 101 into exact alignment.

What is claimed is:

1. An orthopedic surgical holding device for a correcting rod, comprising:

a bone plate for fastening onto a bone, said bone plate defining a proximal side, a distal side and a center line;

a receiver device mounted to said bone plate for receiving the correcting rod, said receiver device having a collar and a outer surface on its end; and a fixing device mounted to said receiver device for maintaining the correcting rod in said receiver device, wherein said bone plate includes a bearing which engages said receiver device such that said receiver device extends through said bearing from said proximal side beyond said distal side of said bone plate where it receives the correcting rod, such that said outer surface assumes a position that is one of a recessed position relative to said proximal side and a flush position relative to said proximal side, and such that said bone plate can be fixed to the bone independently of said receiver device.

2. The orthopedic surgical holding device as defined in claim 1, wherein said receiver device is rotatably disposed in said bearing.

3. The orthopedic surgical holding device as defined in claim 1, wherein said bone plate defines a through opening through which said receiver device extends and about which said bearing is mounted; and wherein said receiver device is maintained radially immovable in said through opening.

4. The orthopedic surgical holding device as defined in claim 3, wherein said receiver device is disposed relative to said bearing with crosswise play, and wherein said receiver device can be pushed crosswise in one direction in said bearing.

5. The orthopedic surgical holding device as defined in claim 4, wherein said through opening is in the shape of an elongated hole, and said bearing is also embodied in the shape of an elongated hole, and wherein said receiver device is maintained in said bearing in a crosswise movable manner.

6. The orthopedic surgical holding device as defined in claim 1, wherein said bone plate defines a recess extending from said proximal side to said distal side, and wherein said collar is disposed in said recess and terminates in a recessed manner relative to said proximal side.

7. The orthopedic surgical holding device as defined in claim 1, wherein said bone plate includes a plurality of bearings associated with a respective one of a plurality of receiver devices.

8. The orthopedic surgical holding device as defined in claim 1, wherein said receiver device is embodied as a fork head and said collar is a radially projecting collar disposed at one end of said receiver device which is received in said bone plate and engages said bearing at least partially.

9. The orthopedic surgical holding device as defined in claim 1, further comprising:

a coupling ring for receiving said receiver device.

10. The orthopedic surgical holding device as defined in claim 9, wherein said coupling ring is mounted on the distal side of said bone plate, and wherein the face of said coupling ring facing said distal side of said bone plate includes radial front serrations enclosing said bearing.

11. The orthopedic surgical holding device as defined in claim 9, wherein said coupling ring defines a distal side which has a diagonal groove for receiving the correcting rod.

12. The orthopedic surgical holding device as defined in claim 11, wherein the correcting rod is provided with longitudinal grooves, wherein said diagonal groove is provided with longitudinal notches free of undercuts into which the correcting rod is inserted, and wherein said longitudinal grooves correspond to said longitudinal notches.

13. The orthopedic surgical holding device as defined in claim 1, further comprising:

an intermediate ring which receives said receiver device.

14. The orthopedic surgical holding device as defined in claim 13, wherein said coupling ring defines a proximal side, and wherein said intermediate ring is disposed between said distal side of said bone plate and said proximal side of said coupling ring.

15. The orthopedic surgical holding device as defined in claim 13, wherein the surface of said intermediate ring resting against said bone plate and said distal side of said bone plate each have a front serration which enclose said bearing, wherein said bearing is in the shape of an elongated hole, and wherein said front serrations are respectively formed by parallel notches extending crosswise to the longitudinal extension of said bearing.

16. The orthopedic surgical holding device as defined in claim 12, wherein the surface of said intermediate ring resting against said coupling ring and said proximal side of said coupling ring are each provided with radial front serrations.

17. The orthopedic surgical holding device as defined in claim 13, further comprising:

a connection fixed against relative rotation but axially movable is provided between said receiver device and said coupling ring.

18. The orthopedic surgical holding device as defined in claim 17, further comprising:

a pin, wherein said receiver device includes at least a circumferentially arranged axial groove, wherein said coupling ring includes a radial bore, and wherein said axial groove is engaged by said pin which extends through said radial bore of said coupling ring.

19. The orthopedic surgical holding device as defined in claim 1, wherein said fixing device includes a head nut, said receiver device is embodied as a fork head and said head nut is adapted to be screwed on to said fork head.

20. The orthopedic surgical holding device as defined in claim 19, further comprising:

a fixing screw to coaxially engage said head nut, said fixing screw having at least one of a hexagon socket and a cup point.

21. The orthopedic surgical holding device as defined in claim 1, wherein said bone plate has at least two fastening bores located opposite to one another for receiving a respective bone screw.

22. The orthopedic surgical holding device as defined in claim 21, wherein one of said fastening bores extend obliquely relative to the center line of said bone plane so that the bone screw received therein extends in a direction to converge with the bone screw received in the opposite one of said fastening bores.

23. The orthopedic surgical holding device as defined in claim 21, wherein each fastening bore includes a cup-shaped bearing for the screw head of its respective bone screw.

* * * * *